United States Patent [19]

Stevenson

[11] Patent Number: 5,978,204
[45] Date of Patent: Nov. 2, 1999

[54] CAPACITOR WITH DUAL ELEMENT ELECTRODE PLATES

[75] Inventor: Robert A. Stevenson, Canyon Country, Calif.

[73] Assignee: Maxwell Energy Products, Inc., San Diego, Calif.

[21] Appl. No.: 08/751,903

[22] Filed: Nov. 18, 1996

[51] Int. Cl.⁶ .................................................. H01G 4/005
[52] U.S. Cl. ........................................... 361/303; 361/311
[58] Field of Search ........................... 361/311–313, 303, 361/308.1, 320–321.5, 304

[56] References Cited

U.S. PATENT DOCUMENTS

| | | |
|---|---|---|
| 4,556,929 | 12/1985 | Tanaka et al. . |
| 5,099,387 | 3/1992 | Kato et al. . |
| 5,319,517 | 6/1994 | Nomura et al. ....................... 361/321.4 |
| 5,335,139 | 8/1994 | Numura et al. ....................... 361/321.2 |
| 5,414,588 | 5/1995 | Barbee, Jr. et al. ..................... 361/304 |

*Primary Examiner*—Dean A. Reichard
*Assistant Examiner*—Anthony Dinkins
*Attorney, Agent, or Firm*—Kelly Bauersfeld Lowry & Kelley, LLP

[57] ABSTRACT

An improved capacitor is provided particularly for use in electromagnetic interference (EMI) filter applications, for example, in an implantable medical device such as a heart pacemaker or defibrillator, to accommodate relatively high pulse currents. The capacitor comprises a plurality of active and ground electrode plates interleaved and embedded within a dielectric casing of ceramic or the like with each active and ground plate being defined by a closely spaced pair of conductive plate elements which significantly increase the total area of each electrode plate, and thereby correspondingly increase the current handling capacity of the capacitor.

11 Claims, 4 Drawing Sheets

CAPACITOR WITH DUAL ELEMENT ELECTRODE PLATES

BACKGROUND OF THE INVENTION

This invention relates generally to improvements in capacitor assemblies, particularly of the type used in implantable medical devices such as heart pacemakers and the like to decouple undesired electromagnetic interference (EMI) signals from the device. More specifically, this invention relates to an improved capacitor having a dual element plate configuration for accommodating relatively high pulse currents without degradation or failure. The invention is particularly designed for use in heart pacemakers (bradycardia), defibrillators (tachycardia) and combined pacemaker defibrillator devices.

Ceramic dielectric capacitors are generally known in the art for use in a wide range of electronic circuit applications, for example, for use as charge storage device, a circuit coupling or decoupling device, a filtering device, etc. Such capacitors conventionally comprise a plurality of conductive active and ground electrode plates encased in an alternating stack at a predetermined spacing or gap within a selected dielectric casing material, typically such as a ceramic material formulated to have a selected dielectric constant. The active and ground electrode plates are respectively connected to appropriate conductive termination points or surfaces which facilitate capacitor connection with other elements of an electronic circuit. Exemplary ceramic cased capacitors are shown and described in U.S. Pat. Nos. 4,931,899 and 5,333,095.

In the past, ceramic cased capacitors have been produced by formulating the ceramic casing material into relatively thin sheets. While in a relatively flexible or "green" state before firing, the ceramic sheets are electroded or silk-screened with a refractory metal to define thin conductive plates of selected area. A plurality of these ceramic based sheets with conductive plates thereon are laminated into a stack and then fired to form the sheets into a rigid and dense, substantially monolithic casing structure having the conductive plates embedded therein at a predetermined dielectric spacing.

In operation, the inherent resistance provided by the thin electrode plates results in at least some power loss in the form of plate heating. The plate power loss, and thus the magnitude of plate heating, is a function of electrical current. If the plate current is sufficiently high for even a relatively short period of time, sufficient plate heating can occur to cause capacitor failure, particularly by localized disruption of the thin electrode plates and/or the connections thereof to the conductive termination components. Filter capacitors used in pacemaker and defibrillator applications regularly encounter relatively high pulse inrush currents, and are thus susceptible to overheating and related failures.

One approach to resolving this problem involves increasing the thickness of the electrode plate layers within the capacitor structure. However, a significant increase in capacitor plate thickness is not possible, or desirable or practical through the use of existing electrode plating and silkscreening technologies. Excessively thick electrode plates lead to capacitor plate delamination and related reliability problems. In this regard, it is important for the electrode plates to have a thin and discontinuous structure with ceramic grain growth penetrating through and integrating the entire structure into a rugged monolithic structure. Another approach is to increase the total surface area of the electrode plates, but this concept has required a significant increase in the volumetric size of the capacitor in a manner which is incompatible with many circuit applications.

The present invention overcomes the problems and disadvantages encountered in the prior art by providing an improved ceramic cased capacitor with an embedded electrode plate pattern that is capable of handling significantly higher current loads, without requiring a significant increase in the volumetric capacitor size.

SUMMARY OF THE INVENTION

In accordance with the invention, an improved ceramic cased capacitor is provided with active and ground electrodes arranged in a dual element plate configuration to accommodate higher pulse currents. The dual plate capacitor is particularly adapted for use as a filter capacitor in heart pacemakers and defibrillators and the like.

The improved capacitor comprises a plurality of conductive active and ground electrode plates embedded in an interleaved geometry within a dielectric casing such as a ceramic monolith or the like. Each active and ground plate within the ceramic casing is defined by a closely spaced and substantially parallel pair of thin conductive plate elements. These dual plate elements cooperatively define a single electrode plate of significantly increased total surface area to correspondingly increase the current handling capacity without significantly increasing the total volumetric size of the capacitor structure.

The active and ground electrode plates, each formed as dual plate elements as described, are respectively connected to appropriate conductive termination surfaces for facilitated electrical connection to other circuit components. In one form, the conductive termination surfaces are disposed on opposite or different sides of a rectangular ceramic casing. In another form, the ceramic casing can be constructed in a discoidal configuration with a central bore lined by one of the conductive termination surfaces for suitable connection to a feedthrough terminal pin of the type used as EMI filters in pacemakers and defibrillators and the like.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
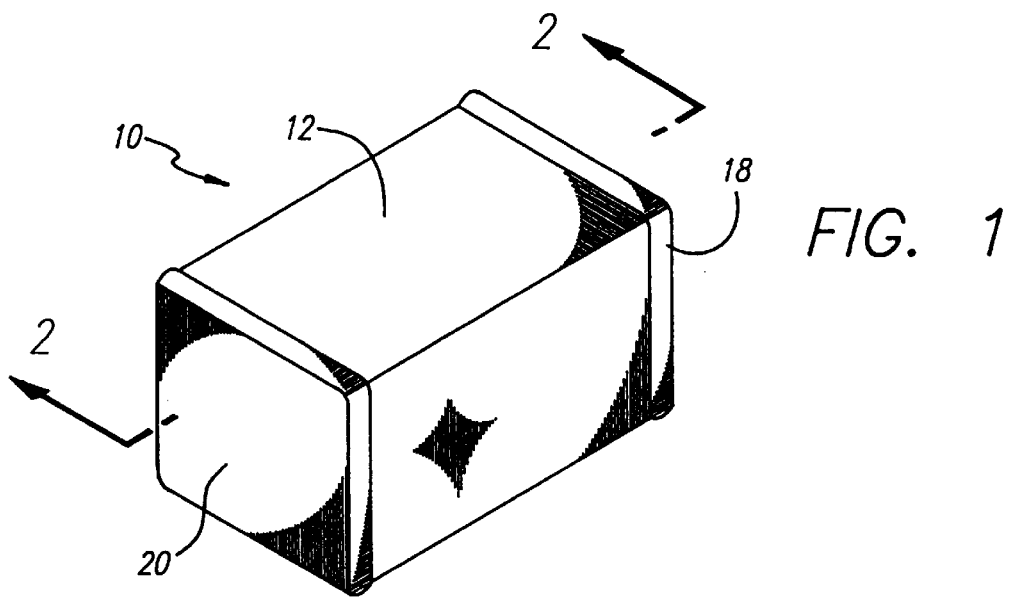
FIG. 1 is a perspective view illustrating a ceramic cased rectangular chip capacitor incorporating a dual element plate configuration in accordance with the novel features of the invention.
Figure 2:
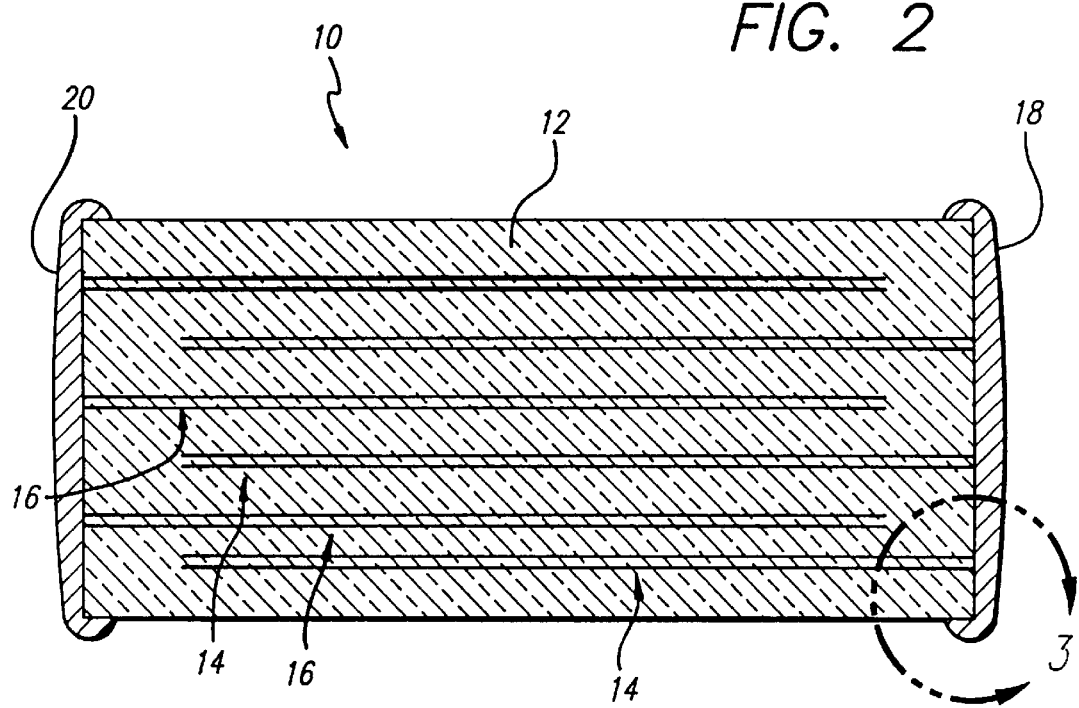
FIG. 2 is an enlarged fragmented sectional view taken generally on the line 2—2 of FIG. 1.
Figure 3:
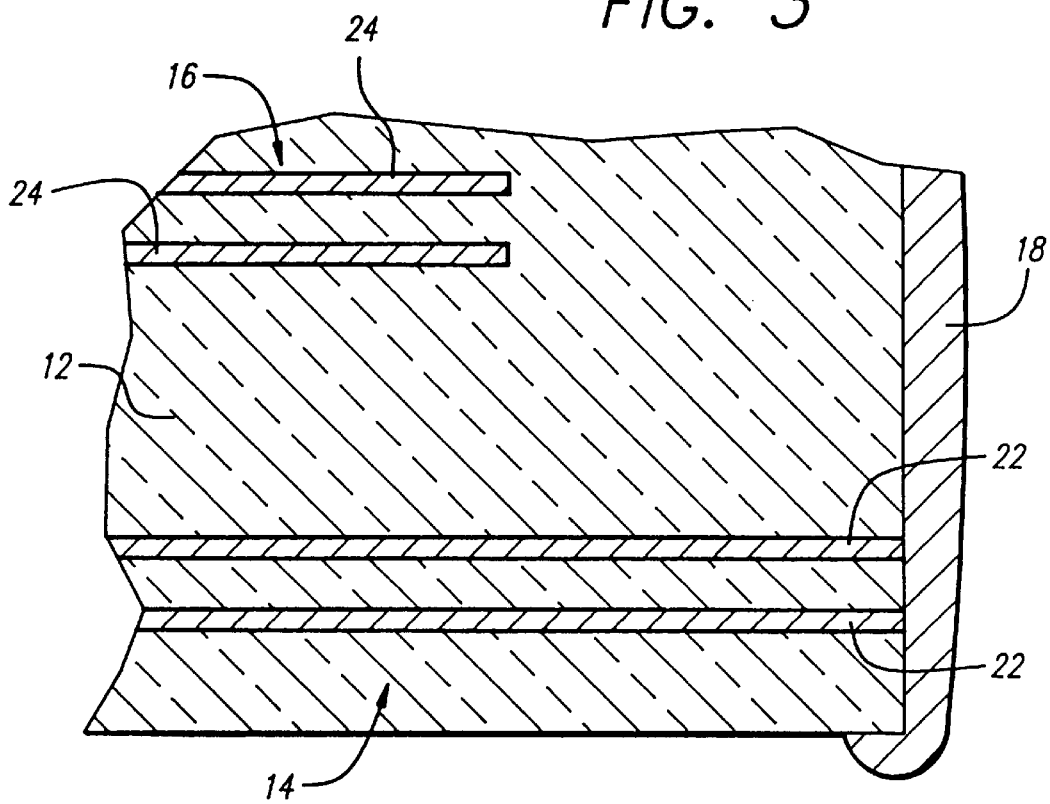
FIG. 3 is a further enlarged fragmented sectional view corresponding generally with the encircled region 3 of FIG. 2.

As shown in the exemplary drawings, a ceramic cased capacitor referred to generally in FIGS. 1–3 by the reference numeral 10, is provided with a novel dual element plate configuration for enhanced peak current carrying capacity. The invention is particularly suited for use in circuit applications which encounter relatively high pulse currents, such as for use as an electromagnetic interference (EMI) filter in an implantable heart pacemaker or defibrillator or the like.

FIGS. 1–3 depict the improved capacitor 10 with a ceramic body or casing 12 constructed substantially in the form of a monolithic block from a selected dielectric and typically ceramic-based material with predetermined dielectric properties. In general, a plurality of active plates 14 and ground plates 16 are embedded within the interior volume of the ceramic casing 12 in a predetermined interleaved and spaced relation. While FIG. 2 shows an illustrative construction with a total of three active plates 14 and a corresponding number of three ground plates 16, it will be understood by persons skilled in the art that the specific number of plates 14, 16 will vary in accordance with the capacitor design, typically to include a significantly larger number of conductive electrode plates. The active plates 14 are electrically connected at one side of the ceramic case 12 to a common conductive termination surface 18, while the ground plates 16 are electrically connected to another conductive termination surface 20 disposed at a different and typically opposite side of the ceramic case 12. In this regard, the conductive plates 14, 16 have appropriate exposed edges at the sides of the ceramic case for facilitated electrical connection to the corresponding termination surfaces 18, 20. Such termination surfaces are formed, as is known in the art, by appropriate surface metalization, or by application of a conductive epoxy or the like.

In accordance with the primary aspect of the invention, each conductive electrode plate 14, 16 is defined by a closely spaced pair of thin conductive plate elements separated in substantially parallel relation by a thin layer of the dielectric casing material. More particularly, as shown best in FIG. 3, each conductive active plate 14 comprises a closely spaced pair of thin conductive plate elements 22, which effectively double the total conductive surface area of the active plate 14. Similarly, each ground plate 16 comprises a corresponding closely spaced pair of thin ground plate elements 24 which also effectively double the total plate surface area. The spacing between the conductive plate element pairs 22, 24, is desirably minimized, such as on the order of about 0.5 to 1.0 mil, whereas the dielectric distance between the interleaved active and ground plates 14, 16, is substantially greater, typically on the order of 5 to 10 mils. With this high voltage configuration, the current carrying capacity of the capacitor 10 is significantly increased with only a small increase in the volumetric size of the capacitor.

In particular, during operation of the capacitor in an electrical circuit, at least some power loss occurs as a result of the inherent resistance of the conductive plates 14, 16 to current flow, thus producing heat.

The conductive plates 14, 16 are typically thin in accordance with silkscreen and/or electroding plate forming processes, sometimes formed as a screen-like matrix, whereby the conductive plates are susceptible to damage and possible failure caused by localized overheating which can change the conductive material to a liquid or plastic like state. The conductive plates 14, 16 must be able to withstand this heat generation without degradation or potential catastrophic failure in accordance with the circuit application.

It is known that the power (P) which must dissipated by each electrode plate 14, 16 is a function of the square of the plate current (I):

$$P = f(I)^2$$

The current load carried by each capacitor plate is a function of the number of plates used in the capacitor. For example, using twice the number electrode plates halves the current carried by each plate in a given circuit application. Thus, by doubling the number of electrode plates, the power which must be dissipated by each plate in the form of heat is reduced by a factor of four. Accordingly, based on power dissipation alone, a capacitor with twice the number of electrode plates has a significantly greater current handling capacity without heat-caused damage. In the past, however, doubling the number of capacitor plates has essentially required a corresponding increase in capacitor size, wherein the requisite size increase is not compatible with certain operating environments.

The present invention resides in the recognition that the number of electrode plates in the capacitor can be effectively doubled to provide significantly improved current handling capacity, but in high voltage applications where the required dielectric spacing is relatively thick, there is only a small increase in the physical size of the capacitor. This is achieved by subdividing each electrode plate 14, 16 into the dual plate elements 22, 24 as described above. With this construction, each active plate element 22 is disposed in the desired and normal dielectric spaced relation with a corresponding ground plate element 24. The only increase in capacitor size for a given number of electrode plates 14, 16 involves the minimal thickness of dielectric material between each pair of dual plate elements 22, 24.

Figure 4:
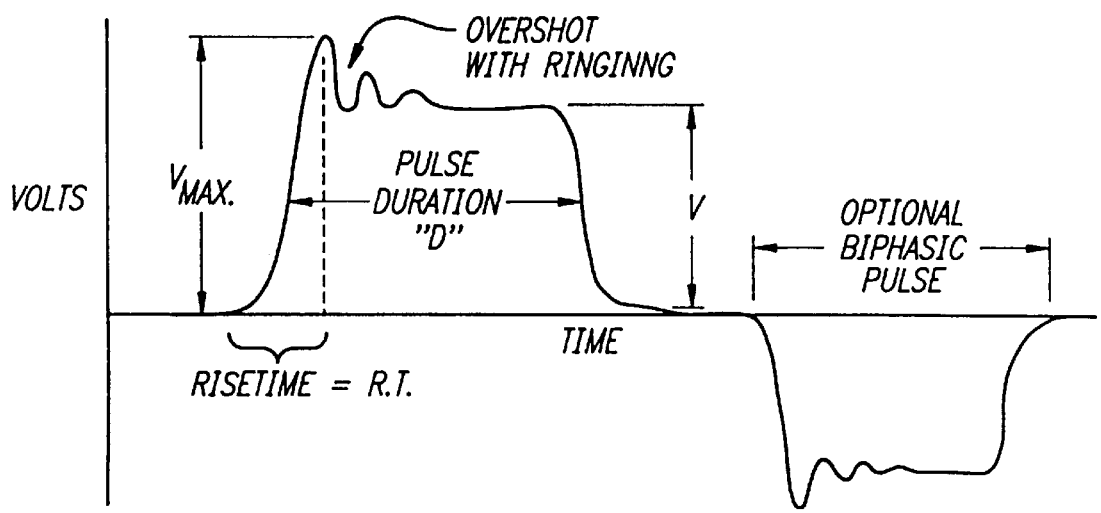
FIG. 4 is a pulse diagram illustrating a typical pulse wave form in a defibrillator application.

The dual plate element capacitor 10 is particularly useful in high voltage pacemaker and defibrillator applications wherein a compact EMI filter capacitor is required to withstand relatively high voltage pulses which often exhibit a transient ringing response. For example, as depicted in FIG. 4, a typical high voltage defibrillation pulse applied to the capacitor can be a substantial voltage on the order of 50 to 750 volts applied with an extremely fast rise time on the order of 50–100 nanoseconds, with a pulse duration of about 10 milliseconds. A short high voltage pulse of this type is frequently accompanied by ringing or overshoot to reach a momentary peak value as high as 1 kilovolt. Peak current loads associated with such high voltage pulses result in substantial heating of the capacitor electrode plates.

Figure 5:
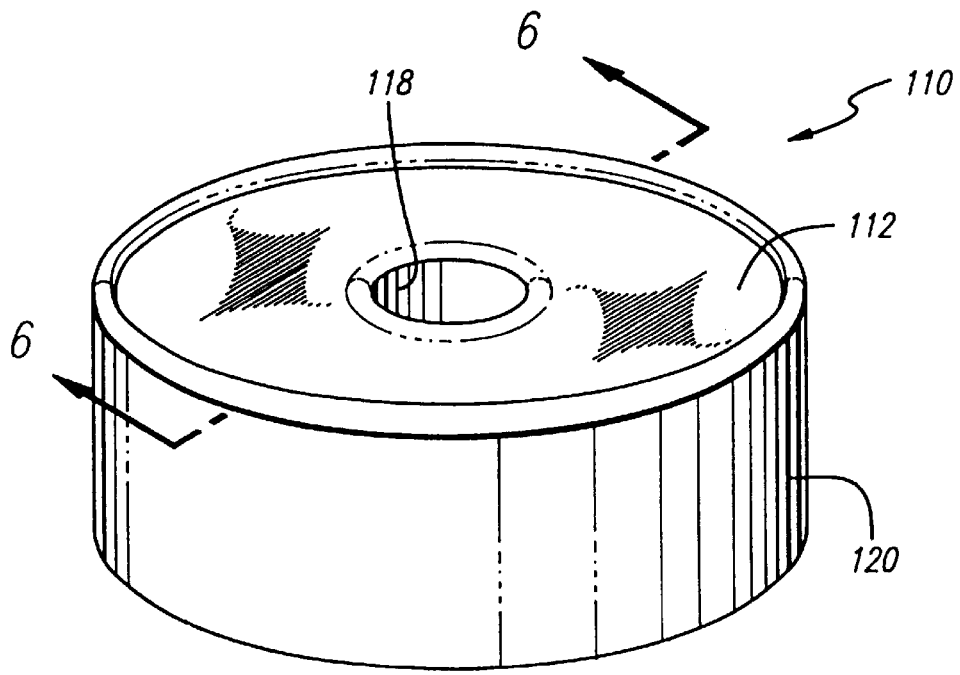
FIG. 5 is a perspective view illustrating the ceramic cased capacitor with dual element plate configuration in an alternative, discoidal form.
Figure 6:
FIG. 6 is an enlarged fragmented sectional view taken generally on the line 6—6 of FIG. 5.

FIGS. 5 and 6 illustrate a modified ceramic cased capacitor 110 with the dual element plate configuration in an alternative geometry, namely, a discoidal (EMI filter) configuration with the active plates 114 electrically connected to a conductive termination surface 118 lining a central bore 26 formed through the ceramic monolith body 112. The ground plates 116 are electrically connected to an associated terminal surface 120 on the outer diameter surface of the discoidal capacitor body. Each active plate 114 is formed as a closely spaced pair of dual plate elements 122, whereas each ground plate 116 is formed as a closely spaced pair of dual plate elements 124. In this configuration, a feedthrough terminal pin of the type shown and described in U.S. Pat. No. 5,333,095 is adapted for insertion through the bore 26 and appropriate conductive attachment to the termination surface 118.

Figure 7:
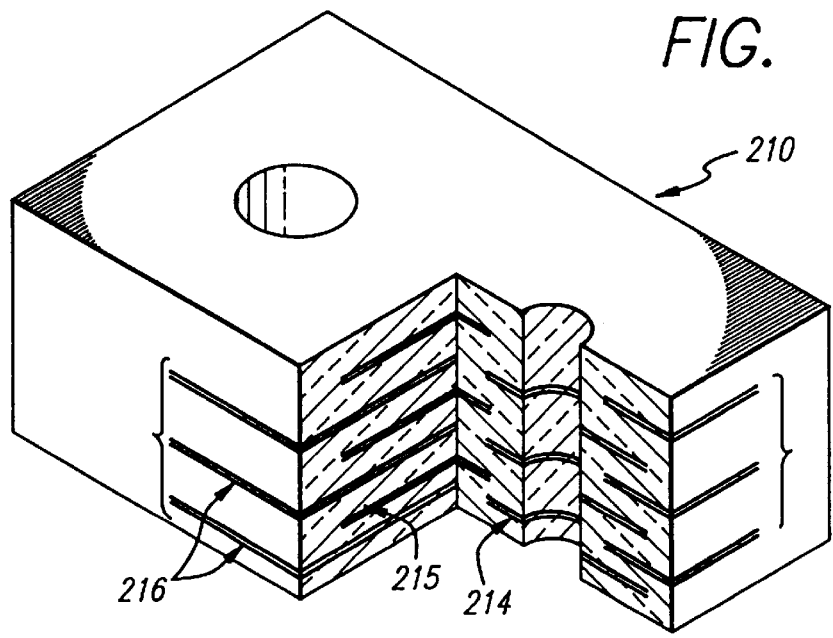
FIG. 7 is a perspective view illustrating a further alternative preferred form of the invention.

FIG. 7 illustrates a further alternative preferred form of the invention, in accordance with the multilayered capacitor geometry shown and described in copending Ser. No. 08/640,098, filed Apr. 30, 1996, entitled EMI FILTER FOR HUMAN IMPLANTABLE HEART DEFIBRILLATORS AND PACEMAKERS and incorporated by reference herein. In this configuration, the modified capacitor 210 has a set of ground plates 216 associated with a group of first active plates 214 and another group of second active plates 215, wherein all of these electrode plates 216, 214, 215, are constructed from pairs of closely spaced conductive plate elements in the same manner as previously described with respect to FIGS. 1–6. The active plate sets 214, 215 are associated respectively with a pair of bores for connection to a corresponding pair of feedthrough terminal pins (not shown) as previously described with respect to FIGS. 5 and 6, whereas the ground plates 216 are adapted for connection to an appropriate ground termination surface (also not shown in FIG. 7).

A variety of further modifications and improvements to the ceramic cased capacitor of the present invention will be apparent to persons skilled in the art. Accordingly, no limitation on the invention is intended by way of the foregoing description and accompanying drawings, except as set forth in the appended claims.

Theory Supporting Dual Element Electrode Plate Design

The conductor resistance, R, in a circuit carrying a current, I, causes an instantaneous power loss in watts, P, equal to:

$$P = I^2 R$$

The cumulative effect of this power loss, is a deposition of energy in the conductor material which raises its temperature. The energy deposition in joules, W, scales like:

$$\Delta W \, P\Delta t \, I^2 R \Delta t$$

where t is the duration of the current pulse in seconds and the temperature change, $\Delta t$, is:

$$\Delta T \, \Delta W/mc$$

where m=mass and c=thermal capacity.

For short pulses where heat loss can be neglected (and change in R with $\Delta T$ is ignored), the accumulation of heat energy can raise conductor temperature to the point where there is a change of state (e.g. solid to liquid to gas) with physical disruption of the conductor and its current carrying capability.

The important parameters determining the effect of current on a material conductor are current density, J, and material resistivity, $\rho$, where:

$$J = I/A, \text{ and}$$

$$\rho = RA/l$$

where: A=the cross sectional area of the conductor and l=the length of the conductor.

The flow of current in a circuit is continuous. The cross sectional area, A, of conductors comprising the circuit may vary but all cross sections carry the same current. Therefore, J and R in circuit elements vary inversely with A.

Figure 8:
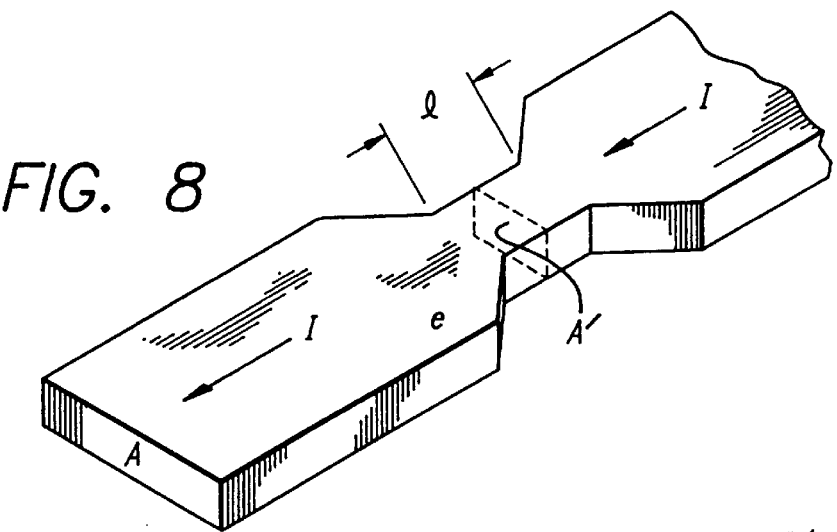
FIGS. 8–10 schematically illustrate the theory supporting the dual element plate configuration of the invention.

This concept is pictorially, illustrated in FIG. 8 which shows a conductor, wherein the resistance of the mid section of the conductor is:

$$R = \rho l/A'$$

The power loss in R is:

$$RI^2 = \rho l I^2/A'$$

multiplied by A'/A' we obtain:

$$RI^2 = J^2 \rho l A'$$

where the current density, $J = I/A$ or, $P = (J^2 \rho)$ (volume at section) where J=constant through A', along l.
then, per unit volume, the energy deposition is:

$$\int_o^T (J(t))^2 \rho \, dt.$$

The magnitude of this quantity must be limited to less than some threshold, W', required for phase change of the conductive material. The intrinsic resistivity property $\rho$ is fixed by the material. Therefore, to conduct a required current I when the energy deposition is going to be too high, a larger cross sectional area is required, thereby affecting power loss and energy deposition like $I/A^2$ for fixed current.

This shows the advantage of increasing the number of paralleled conductors of area A' to carry a current I.

Figure 9:
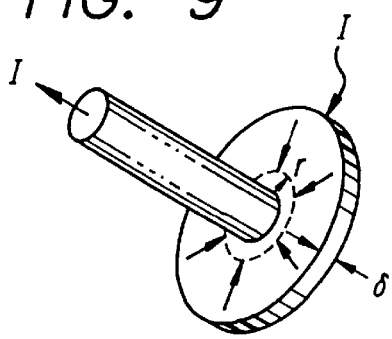

An example of a centrally terminated disc conductor (as in a discoidal capacitor) is shown in FIG. 9. In the case of a disc electrode (conductor) connected to a wire terminal at its center, J is an increasing function of decreasing radius, r, and constant electrode thickness, $\delta$, where:

$$J = I/A = I/2\pi r \delta$$

Figure 10:
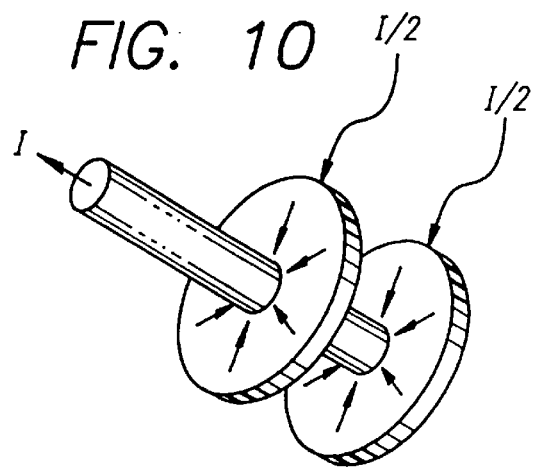

The conductor thickness is typically fixed (by silk screen or equivalent process), and $\rho$ is fixed by the electrode material composition. Therefore, $J^2 \rho$ is highest at the wire connection to the disc. If $\int J^2 \rho dt$ is too high we can decrease J by additional plates, dividing I into paralleled paths (increasing A), as viewed in FIG. 10.

If these discs are imbedded in a capacitor, where I flows through the dielectric as displacement current from opposing electrodes, increasing the number of additional plates is of no benefit above two as the displacement current will not flow to any other than the outermost plates.

What is claimed is:

1. A capacitor assembly, comprising:
   a substantially monolithic casing of dielectric material having a plurality of conductive active and ground electrode plates encased therein in an alternating stack and in predetermined spaced relation;
   each of said active and ground electrode plates comprising a pair of closely spaced conductive plate elements of the same length and separated by a thin layer of dielectric material to preserve the capability of the capacitor assembly to reliably withstand inrush currents from voltage pulses and surges.

2. The capacitor assembly of claim 1 wherein said casing is formed from a ceramic material.

3. The capacitor assembly of claim 1 wherein said casing has a rectangular shape.

4. The capacitor assembly of claim 1 wherein said casing has a discoidal shape.

5. The capacitor assembly of claim 1 further including a first conductive termination surface on said casing and electrically connected to said active electrode plates, and a second conductive termination surface on said casing and electrically connected to said ground electrode plates.

6. The capacitor assembly of claim 1 wherein said active and ground electrode plates are encased within said casing in generally parallel relation with a spacing therebetween of about 5 to 10 mils, and further wherein said pair of conductive plate elements for each of said active and ground electrode plates are encased within said casing in generally parallel relation with a spacing therebetween at about 0.5 to 1.0 mil.

7. A capacitor assembly, comprising:

a substantially monolithic casing of dielectric material having a plurality of conductive active and ground electrode plates encased therein in an alternating stack and in predetermined spaced relation;

a first conductive termination surface on said casing and electrically connected to said active electrode plates; and a second conductive termination surface on said casing and electrically connected to said ground electrode plates;

wherein each of said active and ground electrode plates comprising a pair of closely spaced conductive plate elements of the same length and separated by a thin layer of dielectric material to preserve the capability of the capacitor assembly to reliably withstand inrush currents from voltage pulses and surges.

8. The capacitor assembly of claim 7 wherein said active and ground electrode plates are encased within said casing in generally parallel relation with a spacing therebetween of about 5 to 10 mils, and further wherein said pair of conductive plate elements for each of said active and ground electrode plates are encased within said casing in generally parallel relation with a spacing therebetween at about 0.5 to 1.0 mil.

9. The capacitor assembly of claim 8 wherein said casing is formed from a ceramic material.

10. The capacitor assembly of claim 8 wherein said casing has a rectangular shape.

11. The capacitor assembly of claim 8 wherein said casing has a discoidal shape.

\* \* \* \* \*

UNITED STATES PATENT AND TRADEMARK OFFICE
CERTIFICATE OF CORRECTION

PATENT NO.   : 5,978,204                                                  Page 1 of 1
DATED        : November 2, 1999
INVENTOR(S)  : Robert A. Stevenson It is certified that error appears in the above-identified patent and that said Letters Patent is hereby corrected as shown below:

Column 1,
Line 3, insert the following:
-- This application is a continuation-in-part of U.S. Patent Application Serial No. 08/640,098, filed April 30, 1996 and entitled EMI FILTER FOR HUMAN IMPLANTABLE HEART DEFIBRILLATORS AND PACEMAKERS, now U.S. Patent No. 5,751,539, which claims priority from Provisional Application Serial No. 60/007,581, filed November 27, 1995 entitled EMI FILTER FOR HUMAN IMPLANTABLE HEART DEFIBRILLATORS AND PACEMAKERS --

Signed and Sealed this

Second Day of July, 2002

Attest:

JAMES E. ROGAN
Attesting Officer          Director of the United States Patent and Trademark Office

EX PARTE REEXAMINATION CERTIFICATE (4920th)
United States Patent
Stevenson

(10) Number: US 5,978,204 C1
(45) Certificate Issued: Mar. 23, 2004

(54) CAPACITOR WITH DUAL ELEMENT ELECTRODE PLATES

(75) Inventor: Robert A. Stevenson, Canyon Country, CA (US)

(73) Assignee: GreatBatch-Sierra, Inc., Clarence, NY (US)

Reexamination Request:
No. 90/006,376, Sep. 4, 2002

Reexamination Certificate for:
Patent No.: 5,978,204
Issued: Nov. 2, 1999
Appl. No.: 08/751,903
Filed: Nov. 18, 1996

Certificate of Correction issued Jul. 2, 2002.

Related U.S. Application Data

(63) Continuation-in-part of application No. 08/640,098, filed on Apr. 30, 1996, now Pat. No. 5,751,539.
(60) Provisional application No. 60/007,581, filed on Nov. 27, 1995.

(51) Int. Cl.⁷ .............................................. H01G 4/005
(52) U.S. Cl. ........................................ 361/303; 361/311
(58) Field of Search ............................. 361/311, 301.2, 361/301.4, 302, 303–304

(56) References Cited

U.S. PATENT DOCUMENTS

| | | |
|---|---|---|
| 3,838,320 A | 9/1974 | Klein |
| 4,556,929 A | 12/1985 | Tanaka et al. |
| 4,827,323 A | 5/1989 | Tigelaar et al. |
| 5,040,092 A | 8/1991 | Katho et al. |
| 5,099,387 A | 3/1992 | Kato et al. |
| 5,319,517 A | 6/1994 | Nomura et al. |
| 5,333,095 A * | 7/1994 | Stevenson et al. .......... 361/302 |
| 5,335,139 A | 8/1994 | Nomura et al. |
| 5,414,588 A | 5/1995 | Barbee, Jr. et al. |
| 5,751,539 A | 5/1998 | Stevenson et al. |
| 5,808,856 A | 9/1998 | Bischoff et al. |
| 5,835,339 A | 11/1998 | Sakamoto et al. |
| 6,092,269 A | 7/2000 | Yializis et al. |

FOREIGN PATENT DOCUMENTS

| | | |
|---|---|---|
| DE | 754-894 | 1/1953 |
| DE | 24-45-423 | 7/1975 |
| EP | 276-595 | 8/1988 |
| EP | 312-817 | 4/1989 |
| EP | 455-496 | 11/1991 |
| JP | 50-98656 | 8/1975 |
| JP | 60-254608 | 12/1985 |
| JP | 2-251120 | 10/1990 |
| JP | 6-349666 | 12/1994 |
| JP | 7-7129 | 1/1995 |

\* cited by examiner

*Primary Examiner*—Eric Thomas

(57) ABSTRACT

An improved capacitor is provided particularly for use in electromagnetic interference (EMI) filter applications, for example, in an implantable medical device such as a heart pacemaker or defibrillator, to accommodate relatively high pulse currents. The capacitor comprises a plurality of active and ground electrode plates interleaved and embedded within a dielectric casing of ceramic or the like with each active and ground plate being defined by a closely spaced pair of conductive plate elements which significantly increase the total area of each electrode plate, and thereby correspondingly increase the current handling capacity of the capacitor.

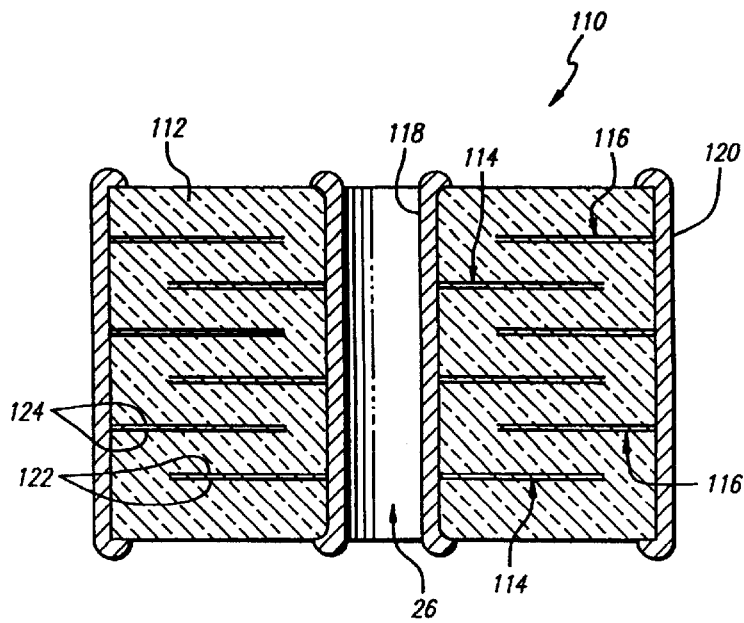

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 5 and 7 are determined to be patentable as amended.

Claims 2–4, 6 and 8–11, dependent on an amended claim, are determined to be patentable.

New claims 12, 13, 14, 15, 16 and 17 are added and determined to be patentable.

1. A capacitor assembly, comprising:
   a substantially monolithic casing of dielectric material having a plurality of conductive active and ground electrode plates encased therein in an alternating stack and in predetermined spaced relation; *and*
   a feedthrough terminal pin extending through a bore in said casing, said feedthrough terminal pin being conductively coupled to said active electrode plates;
   wherein each of said active and ground electrode plates comprising a pair of closely spaced conductive plate elements of the same length and separated by a thin layer of dielectric material to preserve the capability of the capacitor assembly to reliably withstand inrush currents from voltage pulses and surges.

5. The capacitor assembly of claim 1 further including a first conductive termination surface [on said casing] *within said bore* and electrically connected to said active electrode plates, and a second conductive termination surface on said casing and electrically connected to said ground electrode plates.

7. A capacitor assembly, comprising:
   a substantially monolithic casing of dielectric material having a plurality of conductive active and ground electrode plates encased therein in an alternating stack and in predetermined spaced relation;
   *a feedthrough terminal pin extending through a bore in said casing;*
   a first conductive termination surface [on said casing] *within said bore* and electrically [connected] *connecting said feedthrough terminal pin* to said active electrode plates; and
   a second conductive termination surface on said casing and electrically connected to said ground electrode plates;
   wherein each of said active and ground electrode plates [comprising] *comprises* a pair of closely spaced conductive plate elements of the same length and separated by a thin layer of dielectric material to preserve the capability of the capacitor assembly to reliably withstand inrush currents from voltage pulses and surges.

*12. The capacitor assembly of claim 1 configured for use in an EMI filter in an implantable heart pacemaker or defibrillator.*

*13. The capacitor assembly of claim 7 configured for use in an EMI filter in an implantable heart pacemaker.*

*14. The capacitor assembly of claim 8 configured for use in an EMI filter in an implantable heart defibrillator.*

*15. A feedthrough capacitor assembly configured for use in an EMI filter in an implantable heart pacemaker or defibrillator, comprising:*
   *a substantially monolithic casing of dielectric material having a plurality of conductive active and ground electrode plates encased therein in an alternating stack and in predetermined spaced relation;*
   *a feedthrough terminal pin extending through a bore in said casing;*
   *a first conductive termination surface within said bore and conductively coupling said feedthrough terminal pin to said active electrode plates; and*
   *a second conductive termination surface on said casing and conductivity coupled to said ground electrode plates;*
   *wherein each of said active and ground electrode plates comprises a pair of closely spaced conductive plate elements of the same length and separated by a thin layer of dielectric material to preserve the capability of the capacitor assembly to reliably withstand inrush currents from voltage pulses and surges.*

*16. The capacitor assembly of claim 15, wherein said casing is formed from a ceramic material.*

*17. The capacitor assembly of claim 15, wherein said active and ground electrode plates are encased within said casing in generally parallel relation with a spacing therebetween of about 5 to 10 mils, and further wherein said pair of conductive plate elements for each of said active and ground electrode plates are encased within said casing in generally parallel relation with a spacing therebetween at about 0.5 to 1.0 mil.*

\* \* \* \* \*